United States Patent
Albert et al.

(10) Patent No.: US 6,251,617 B1
(45) Date of Patent: Jun. 26, 2001

(54) GLYCINE TRANSPORTER

(75) Inventors: Vivian R. Albert, Montclair; Leslie R. Z. Kowalski, Cedar Knolls, both of NJ (US)

(73) Assignee: Allelix Neuroscience, Inc.

(*) Notice: Subject to any disclaimer, the term of this patent is extended or adjusted under 35 U.S.C. 154(b) by 0 days.

(21) Appl. No.: 09/396,177

(22) Filed: Sep. 14, 1999

Related U.S. Application Data

(62) Division of application No. 08/834,467, filed on Apr. 11, 1997, now Pat. No. 6,008,015.

(51) Int. Cl.[7] .............................. C07K 1/00; G01N 33/53; G01N 33/566
(52) U.S. Cl. .................... 435/7.8; 435/70.1; 435/325; 435/252.3; 435/254.11; 436/501; 436/804; 530/350
(58) Field of Search ............................. 530/350; 514/12; 435/7.2, 7.21, 7.8, 70.11, 325, 252.3, 254.11; 436/501, 503, 504, 804; 424/185.1

(56) References Cited

U.S. PATENT DOCUMENTS

| | | |
|---|---|---|
| 5,188,954 | 2/1993 | Lam et al. . |
| 5,424,185 | 6/1995 | Lam et al. . |

OTHER PUBLICATIONS

Olivares et al. Carboxyl Terminus of the Glycine Transporter GlYTI is Necessary for Corred Processing of the Protein J. Biol. Chem. 269: 28400–28404, 1994.*
Shi et al. Stable Inducible Expression of a Functional Rat Liver Organic Anion Transport Protein in Hela Cells J. Biol. Chem. 270: 25591–25595, 1995.*
Lebo et al in "Cold Spring Harbor Symposium on Quantitative Biology" vol. L1 Molecular Biology of Homosapens, Cold Spring Harbor Laboratory 1986, pp. 169–176.*
Johnson and Ascher, Nature, 325: 529–531, 1987.
Fletcher et al., Glycine Neurotransmission, Otterson and Storm–Mathisen, eds., 1990, pp. 193–219.
Smith et al., Neuron, 8: 927–935, 1992.
Liu et al., J. Biol. Chem., 268:22802–22808, 1993.
Jursky and Nelson, J. Neurochemistry, 64:1026–1033, 1995.
Uhl, Trends in Neuroscience, 15:265–268, 1992.
Clark and Amara, BioEssays, 15:323–332, 1993.
Yaksh, Pain, 111–123, 1989.
Truong et al., Movement Disorders, 3:77–87, 1988.
Becker, FASEB Journal, 4:2767–2774, 1990.
Lopez–Corcuera et al., J. Biol. Chem., 266:24809–24814, 1991.
Liu et al., FEBS Letters, 305:110–114, 1992.
Bannon et al., J. Neurochem., 54:706–708, 1990.
Guastella et al., Science, 249:1303–1306, 1990.
Grimwood et al., Molecular Pharmacology, 49:923–930, 1992.
Kim et al., Molecular Pharmacology, 45:608–617, 1994.
Lu et al., Proc. Nat'l. Acad. Sci. USA, 88:6289–6292, 1991.
White et al., J. Neurochemistry, 35:503–512, 1989.
Becker et al., J. Neuroscience, 6:1358–1364, 1986.
Adams et al., J. Neuroscience, 15:2524–2532, 1995.
Zafra et al., J. Neuroscience, 15:3952–3969, 1995.
Zafra et al., Eur. Neuroscience, 7:1342–1352, 1995.
Goebel, D.J., Mol. Brain Res., 40:139–142, 1996.
Jursky et al., J. Neurochem, 67:336–344, 1996.
Borowsky et al., Neuron, 10:851–863, 1993.
Guastella et al., Proc. Nat'l. Acad. Sci. USA 89:7189–7193, 1992.
Blakely et al., Proc. Nat'l. Acad., Sci. USA 85:9846–9850, 1988.

* cited by examiner

Primary Examiner—Patricia A. Duffy
(74) Attorney, Agent, or Firm—Dechert

(57) ABSTRACT

Provided are, among other things, nucleic acid sequences encoding the GlyT1d form of glycine transporter, vectors, methods of producing the transporter, and methods for identifying bioactive agents.

12 Claims, 6 Drawing Sheets

```
1    GGGCCGGGGGCTGCAGCATGCTCTTGAGATCTGTGGCCTGAAAGGCGCTGGAAGCAGAGC    60

61   CTGTGAGTGTGGTCCCCGTCACCAGAGCCCCAACCCACCGCCGCCATGGTAGGAAAAGGT    120
                                                    M  V  G  K  G

121  GCCAAAGGGATGCTGGTGACGCTTCTCCCTGTTCAGAGATCCTTCTTCCTGCCACCCTTT    180
     A  K  G  M  L  V  T  L  L  P  V  Q  R  S  F  F  L  P  P  F
                 10                            20

181  TCTGGAGCCACTCCCTCTACTTCCCTAGCAGAGTCTGTCCTCAAAGTCTGGCATGGGGCC    240
     S  G  A  T  P  S  T  S  L  A  E  S  V  L  K  V  W  H  G  A
                 30                            40

241  TACAACTCTGGTCTCCTTCCCCAACTCATGGCCCAGCACTCCCTAGCCATGGCCCAGAAT    300
     Y  N  S  G  L  L  P  Q  L  M  A  Q  H  S  L  A  M  A  Q  N
                 50                            60

301  GGTGCTGTGCCCAGCGAGGCCACCAAGAGGGACCAGAACCTCAAACGGGGCAACTGGGGC    360
     G  A  V  P  S  E  A  T  K  R  D  Q  N  L  K  R  G  N  W  G
                 70                            80

361  AACCAGATCGAGTTTGTACTGACGAGCGTGGGCTATGCCGTGGGCCTGGGCAATGTCTGG    420
     N  Q  I  E  F  V  L  T  S  V  G  Y  A  V  G  L  G  N  V  W
                 90                            100

421  CGCTTCCCATACCTCTGCTATCGCAACGGGGGAGGCGCCTTCATGTTCCCCTACTTCATC    480
     R  F  P  Y  L  C  Y  R  N  G  G  G  A  F  M  F  P  Y  F  I
                 110                           120

481  ATGCTCATCTTCTGCGGGATCCCCCTCTTCTTCATGGAGCTCTCCTTCGGCCAGTTTGCA    540
     M  L  I  F  C  G  I  P  L  F  F  M  E  L  S  F  G  Q  F  A
                 130                           140

541  AGCCAGGGGTGCCTGGGGGTCTGGAGGATCAGCCCCATGTTCAAAGGAGTGGGCTATGGT    600
     S  Q  G  C  L  G  V  W  R  I  S  P  M  F  K  G  V  G  Y  G
                 150                           160
```

FIG. 1A

```
601  ATGATGGTGGTGTCCACCTACATCGGCATCTACTACAATGTGGTCATCTGCATCGCCTTC  660
      M   M   V   V   S   T   Y   I   G   I   Y   Y   N   V   V   I   C   I   A   F
                     170                                 180

661  TACTACTTCTTCTCGTCCATGACGCACGTGCTGCCCTGGGCCTACTGCAATAACCCCTGG  720
      Y   Y   F   F   S   S   M   T   H   V   L   P   W   A   Y   C   N   N   P   W
                     290                                 200

721  AACACGCATGACTGCGCCGGTGTACTGGACGCCTCCAACCTCACCAATGGCTCTCGGCCA  780
      N   T   H   D   C   A   G   V   L   D   A   S   N   L   T   N   G   S   R   P
                     210                                 220

781  GCCGCCTTGCCCAGCAACCTCTCCCACCTGCTCAACCACAGCCTCCAGAGGACCAGCCCC  840
      A   A   L   P   S   N   L   S   H   L   L   N   H   S   L   Q   R   T   S   P
                     230                                 240

841  AGCGAGGAGTACTGGAGGCTGTACGTGCTGAAGCTGTCAGATGACATTGGGAACTTTGGG  900
      S   E   E   Y   W   R   L   Y   V   L   K   L   S   D   D   I   G   N   F   G
                     250                                 260

901  GAGGTGCGGCTGCCCCTCCTTGGCTGCCTCGGTGTCTCCTGGTTGGTCGTCTTCCTCTGC  960
      E   V   R   L   P   L   L   G   C   L   G   V   S   W   L   V   V   F   L   C
                     270                                 280

961  CTCATCCGAGGGGTCAAGTCTTCAGGGAAAGTGGTGTACTTCACGGCCACGTTCCCCTAC 1020
      L   I   R   G   V   K   S   S   G   K   V   V   Y   F   T   A   T   F   P   Y
                     290                                 300

1021 GTGGTGCTGACCATTCTGTTTGTCCGCGGAGTGACCCTGGAGGGAGCCTTTGACGGCATC 1080
      V   V   L   T   I   L   F   V   R   G   V   T   L   E   G   A   F   D   G   I
                     310                                 320

1081 ATGTACTACCTAACCCCGCAGTGGGACAAGATCCTGGAGGCCAAGGTGTGGGGTGATGCT 1140
      M   Y   Y   L   T   P   Q   W   D   K   I   L   E   A   K   V   W   G   D   A
                     330                                 340

1141 GCCTCCCAGATCTTCTACTCACTGGCGTGCGCGTGGGGAGGCCTCATCACCATGGCTTCC 1200
      A   S   Q   I   F   Y   S   L   A   C   A   W   G   G   L   I   T   M   A   S
                     350                                 360
```

FIG. 1B

```
1201 TACAACAAGTTCCACAATAACTGTTACCGGGACAGTGTCATCATCAGCATCACCAACTGT 1260
      Y  N  K  F  H  N  N  C  Y  R  D  S  V  I  I  S  I  T  N  C
                  370                            380

1261 GCCACCAGCGTCTATGCTGGCTTCGTCATCTTCTCCATCCTCGGCTTCATGGCCAATCAC 1320
      A  T  S  V  Y  A  G  F  V  I  F  S  I  L  G  F  M  A  N  H
                  390                            400

1321 CTGGGCGTGGATGTGTCCCGTGTGGCAGACCACGGCCCTGGCCTGGCCTTCGTGGCTTAC 1380
      L  G  V  D  V  S  R  V  A  D  H  G  P  G  L  A  F  V  A  Y
                  410                            420

1381 CCCGAGGCCCTCACACTACTTCCCATCTCCCCGCTGTGGTCTCTGCTCTTCTTCTTCATG 1440
      P  E  A  L  T  L  L  P  I  S  P  L  W  S  L  L  F  F  F  M
                  430                            440

1441 CTTATCCTGCTGGGGCTGGGCACTCAGTTCTGCCTCCTGGAGACGCTGGTCACAGCCATT 1500
      L  I  L  L  G  L  G  T  Q  F  C  L  L  E  T  L  V  T  A  I
                  450                            460

1501 GTGGATGAGGTGGGGAATGAGTGGATCCTGCAGAAAAAGACCTATGTGACCTTGGGCGTG 1560
      V  D  E  V  G  N  E  W  I  L  Q  K  K  T  Y  V  T  L  G  V
                  470                            480

1561 GCTGTGGCTGGCTTCCTGCTGGGCATCCCCCTCACCAGCCAGGCAGGCATCTATTGGCTG 1620
      A  V  A  G  F  L  L  G  I  P  L  T  S  Q  A  G  I  Y  W  L
                  490                            500

1621 CTGCTGATGGACAACTATGCGGCCAGCTTCTCCTTGGTGGTCATCTCCTGCATCATGTGT 1680
      L  L  M  D  N  Y  A  A  S  F  S  L  V  V  I  S  C  I  M  C
                  510                            520

1681 GTGGCCATCATGTACATCTACGGGCACCGGAACTACTTCCAGGACATCCAGATGATGCTG 1740
      V  A  I  M  Y  I  Y  G  H  R  N  Y  F  Q  D  I  Q  M  M  L
                  530                            540

1741 GGATTCCCACCACCCCTCTTCTTTCAGATCTGCTGGCGCTTCGTCTCTCCCGCCATCATC 1800
      G  F  P  P  P  L  F  F  Q  I  C  W  R  F  V  S  P  A  I  I
                  550                            560
```

FIG. 1C

```
1801 TTCTTTATTCTAGTTTTCACTGTGATCCAGTACCAGCCGATCACCTACAACCACTACCAG 1860
      F   F   I   L   V   F   T   V   I   Q   Y   Q   P   I   T   Y   N   H   Y   Q
                          570                                 580

1861 TACCCAGGCTGGGCCGTGGCCATTGGCTTCCTCATGGCTCTGTCCTCCGTCCTCTGCATC 1920
      Y   P   G   W   A   V   A   I   G   F   L   M   A   L   S   S   V   L   C   I
                          590                                 600

1921 CCCCTCTACGCCATGTTCCGGCTCTGCCGCACAGACGGGGACACCCTCCTCCAGCGTTTG 1980
      P   L   Y   A   M   F   R   L   C   R   T   D   G   D   T   L   L   Q   R   L
                          610                                 620

1981 AAAAATGCCACAAAGCCAAGCAGAGACTGGGGCCCTGCCCTCCTGGAGCACCGGACAGGG 2040
      K   N   A   T   K   P   S   R   D   W   G   P   A   L   L   E   H   R   T   G
                          630                                 640

2041 CGCTACGCCCCCACCATAGCCCCCTCTCCTGAGGACGGCTTCGAGGTCCAGTCACTGCAC 2100
      R   Y   A   P   T   I   A   P   S   P   E   D   G   F   E   V   Q   S   L   H
                          650                                 660

2101 CCGGACAAGGCGCAGATCCCCATTGTGGGCAGTAATGGCTCCAGCCGCCTCCAGGACTCC 2160
      P   D   K   A   Q   I   P   I   V   G   S   N   G   S   S   R   L   Q   D   S
                          670                                 680

2161 CGGATATAGCACAGCTGCCAGGGGAGTGCCACCTCTAGA                      2199
      R   I   *
```

FIG. 1D

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 2064 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

| | | | | | |
|---|---|---|---|---|---|
| ATGGTAGGAA | AAGGTGCCAA | AGGGATGCTG | GTGACGCTTC | TCCCTGTTCA | GAGATCCTTC | 60 |
| TTCCTGCCAC | CCTTTTCTGG | AGCCACTCCC | TCTACTTCCC | TAGCAGAGTC | TGTCCTCAAA | 120 |
| GTCTGGCATG | GGGCCTACAA | CTCTGGTCTC | CTTCCCAAC | TCATGGCCCA | GCACTCCCTA | 180 |
| GCCATGGCCC | AGAATGGTGC | TGTGCCCAGC | GAGGCCACCA | AGAGGGACCA | GAACCTCAAA | 240 |
| CGGGGCAACT | GGGCAACCA | GATCGAGTTT | GTACTGACGA | GCGTGGGCTA | TGCCGTGGGC | 300 |
| CTGGGCAATG | TCTGGCGCTT | CCCATACCTC | TGCTATCGCA | ACGGGGAGG | CGCCTTCATG | 360 |
| TTCCCCTACT | TCATCATGCT | CATCTTCTGC | GGGATCCCCC | TCTTCTTCAT | GGAGCTCTCC | 420 |
| TTCGGCCAGT | TTGCAAGCCA | GGGGTGCCTG | GGGGTCTGGA | GGATCAGCCC | CATGTTCAAA | 480 |
| GGAGTGGGCT | ATGGTATGAT | GGTGGTGTCC | ACCTACATCG | GCATCTACTA | CAATGTGGTC | 540 |
| ATCTGCATCG | CCTTCTACTA | CTTCTTCTCG | TCCATGACGC | ACGTGCTGCC | CTGGGCCTAC | 600 |
| TGCAATAACC | CCTGGAACAC | GCATGACTGC | GCCGGTGTAC | TGGACGCCTC | CAACCTCACC | 660 |
| AATGGCTCTC | GGCCAGCCGC | CTTGCCCAGC | AACCTCTCCC | ACCTGCTCAA | CCACAGCCTC | 720 |
| CAGAGGACCA | GCCCCAGCGA | GGAGTACTGG | AGGCTGTACG | TGCTGAAGCT | GTCAGATGAC | 780 |
| ATTGGGAACT | TTGGGGAGGT | GCGGCTGCCC | CTCCTTGGCT | GCCTCGGTGT | CTCCTGGTTG | 840 |
| GTCGTCTTCC | TCTGCCTCAT | CCGAGGGGTC | AAGTCTTCAG | GGAAAGTGGT | GTACTTCACG | 900 |
| GCCACGTTCC | CCTACGTGGT | GCTGACCATT | CTGTTTGTCC | GCGGAGTGAC | CCTGGAGGGA | 960 |
| GCCTTTGACG | GCATCATGTA | CTACCTAACC | CCGCAGTGGG | ACAAGATCCT | GGAGGCCAAG | 1020 |
| GTGTGGGGTG | ATGCTGCCTC | CCAGATCTTC | TACTCACTGG | CGTGCGCGTG | GGGAGGCCTC | 1080 |
| ATCACCATGG | CTTCCTACAA | CAAGTTCCAC | AATAACTGTT | ACCGGGACAG | TGTCATCATC | 1140 |
| AGCATCACCA | ACTGTGCCAC | CAGCGTCTAT | GCTGGCTTCG | TCATCTTCTC | CATCCTCGGC | 1200 |
| TTCATGGCCA | ATCACCTGGG | CGTGGATGTG | TCCCGTGTGG | CAGACCACGG | CCCTGGCCTG | 1260 |
| GCCTTCGTGG | CTTACCCCGA | GGCCCTCACA | CTACTTCCCA | TCTCCCCGCT | GTGGTCTCTG | 1320 |
| CTCTTCTTCT | TCATGCTTAT | CCTGCTGGGG | CTGGGCACTC | AGTTCTGCCT | CCTGGAGACG | 1380 |
| CTGGTCACAG | CCATTGTGGA | TGAGGTGGGG | AATGAGTGGA | TCCTGCAGAA | AAAGACCTAT | 1440 |
| GTGACCTTGG | GCGTGGCTGT | GGCTGGCTTC | CTGCTGGGCA | TCCCCCTCAC | CAGCCAGGCA | 1500 |
| GGCATCTATT | GGCTGCTGCT | GATGGACAAC | TATGCGGCCA | GCTTCTCCTT | GGTGGTCATC | 1560 |
| TCCTGCATCA | TGTGTGTGGC | CATCATGTAC | ATCTACGGGC | ACCGGAACTA | CTTCCAGGAC | 1620 |
| ATCCAGATGA | TGCTGGGATT | CCCACCACCC | TCTTCTTTC | AGATCTGCTG | GCGCTTCGTC | 1680 |
| TCTCCCGCCA | TCATCTTCTT | TATTCTAGTT | TTCACTGTGA | TCCAGTACCA | GCCGATCACC | 1740 |
| TACAACCACT | ACCAGTACCC | AGGCTGGGCC | GTGGCCATTG | GCTTCCTCAT | GGCTCTGTCC | 1800 |
| TCCGTCCTCT | GCATCCCCCT | CTACGCCATG | TTCCGGCTCT | GCCGCACAGA | CGGGGACACC | 1860 |
| CTCCTCCAGC | GTTTGAAAAA | TGCCACAAAG | CCAAGCAGAG | ACTGGGGCCC | TGCCCTCCTG | 1920 |
| GAGCACCGGA | CAGGGCGCTA | CGCCCCCACC | ATAGCCCCCT | CTCCTGAGGA | CGGCTTCGAG | 1980 |
| GTCCAGTCAC | TGCACCCGGA | CAAGGCGCAG | ATCCCCATTG | TGGGCAGTAA | TGGCTCCAGC | 2040 |
| CGCCTCCAGG | ACTCCCGGAT | ATAG | | | | 2064 |

(2) INFORMATION FOR SEQ ID NO:2:

(i) SEQUENCE CHARACTERISTICS:
        (A) LENGTH: 687 amino acids (B) TYPE: amino acid
(C) STRANDEDNESS: single
(D) TOPOLOGY: linear (xi) SEQUENCE DESCRIPTION: SEQ ID NO:2:

```
Met Val Gly Lys Gly Ala Lys Gly Met Leu Val Thr Leu Leu Pro Val
 1               5                  10                  15

Gln Arg Ser Phe Phe Leu Pro Pro Phe Ser Gly Ala Thr Pro Ser Thr
            20                  25                  30

Ser Leu Ala Glu Ser Val Leu Lys Val Trp His Gly Ala Tyr Asn Ser
        35                  40                  45

Gly Leu Leu Pro Gln Leu Met Ala Gln His Ser Leu Ala Met Ala Gln
50                  55                  60

Asn Gly Ala Val Pro Ser Glu Ala Thr Lys Arg Asp Gln Asn Leu Lys
65                  70                  75                  80

Arg Gly Asn Trp Gly Asn Gln Ile Glu Phe Val Leu Thr Ser Val Gly
                85                  90                  95

Tyr Ala Val Gly Leu Gly Asn Val Trp Arg Phe Pro Tyr Leu Cys Tyr
            100                 105                 110

Arg Asn Gly Gly Gly Ala Phe Met Phe Pro Tyr Phe Ile Met Leu Ile
            115                 120                 125

Phe Cys Gly Ile Pro Leu Phe Phe Met Glu Leu Ser Phe Gly Gln Phe
130                 135                 140

Ala Ser Gln Gly Cys Leu Gly Val Trp Arg Ile Ser Pro Met Phe Lys
145                 150                 155                 160

Gly Val Gly Tyr Gly Met Met Val Val Ser Thr Tyr Ile Gly Ile Tyr
                165                 170                 175

Tyr Asn Val Val Ile Cys Ile Ala Phe Tyr Tyr Phe Phe Ser Ser Met
            180                 185                 190

Thr His Val Leu Pro Trp Ala Tyr Cys Asn Asn Pro Trp Asn Thr His
            195                 200                 205

Asp Cys Ala Gly Val Leu Asp Ala Ser Asn Leu Thr Asn Gly Ser Arg
    210                 215                 220

Pro Ala Ala Leu Pro Ser Asn Leu Ser His Leu Leu Asn His Ser Leu
225                 230                 235                 240

Gln Arg Thr Ser Pro Ser Glu Glu Tyr Trp Arg Leu Tyr Val Leu Lys
            245                 250                 255

Leu Ser Asp Asp Ile Gly Asn Phe Gly Glu Val Arg Leu Pro Leu Leu
            260                 265                 270

Gly Cys Leu Gly Val Ser Trp Leu Val Val Phe Leu Cys Leu Ile Arg
            275                 280                 285

Gly Val Lys Ser Ser Gly Lys Val Val Tyr Phe Thr Ala Thr Phe Pro
            290                 295                 300

Tyr Val Val Leu Thr Ile Leu Phe Val Arg Gly Val Thr Leu Glu Gly
305                 310                 315                 320

Ala Phe Asp Gly Ile Met Tyr Tyr Leu Thr Pro Gln Trp Asp Lys Ile
            325                 330                 335

Leu Glu Ala Lys Val Trp Gly Asp Ala Ala Ser Gln Ile Phe Tyr Ser
            340                 345                 350

Leu Ala Cys Ala Trp Gly Gly Leu Ile Thr Met Ala Ser Tyr Asn Lys
            355                 360                 365

Phe His Asn Asn Cys Tyr Arg Asp Ser Val Ile Ile Ser Ile Thr Asn
            370                 375                 380

Cys Ala Thr Ser Val Tyr Ala Gly Phe Val Ile Phe Ser Ile Leu Gly
```

```
385                 390                 395                 400
Phe Met Ala Asn His Leu Gly Val Asp Val Ser Arg Val Ala Asp His
                405                 410                 415
Gly Pro Gly Leu Ala Phe Val Ala Tyr Pro Glu Ala Leu Thr Leu Leu
                420                 425                 430
Pro Ile Ser Pro Leu Trp Ser Leu Leu Phe Phe Phe Met Leu Ile Leu
                435                 440                 445
Leu Gly Leu Gly Thr Gln Phe Cys Leu Leu Glu Thr Leu Val Thr Ala
            450                 455                 460
Ile Val Asp Glu Val Gly Asn Glu Trp Ile Leu Gln Lys Lys Thr Tyr
465                 470                 475                 480
Val Thr Leu Gly Val Ala Val Ala Gly Phe Leu Leu Gly Ile Pro Leu
                485                 490                 495
Thr Ser Gln Ala Gly Ile Tyr Trp Leu Leu Leu Met Asp Asn Tyr Ala
                500                 505                 510
Ala Ser Phe Ser Leu Val Val Ile Ser Cys Ile Met Cys Val Ala Ile
                515                 520                 525
Met Tyr Ile Tyr Gly His Arg Asn Tyr Phe Gln Asp Ile Gln Met Met
        530                 535                 540
Leu Gly Phe Pro Pro Pro Leu Phe Phe Gln Ile Cys Trp Arg Phe Val
545                 550                 555                 560
Ser Pro Ala Ile Ile Phe Phe Ile Leu Val Phe Thr Val Ile Gln Tyr
                565                 570                 575
Gln Pro Ile Thr Tyr Asn His Tyr Gln Tyr Pro Gly Trp Ala Val Ala
                580                 585                 590
Ile Gly Phe Leu Met Ala Leu Ser Ser Val Leu Cys Ile Pro Leu Tyr
            595                 600                 605
Ala Met Phe Arg Leu Cys Arg Thr Asp Gly Asp Thr Leu Leu Gln Arg
        610                 615                 620
Leu Lys Asn Ala Thr Lys Pro Ser Arg Asp Trp Gly Pro Ala Leu Leu
625                 630                 635                 640
Glu His Arg Thr Gly Arg Tyr Ala Pro Thr Ile Ala Pro Ser Pro Glu
                645                 650                 655
Asp Gly Phe Glu Val Gln Ser Leu His Pro Asp Lys Ala Gln Ile Pro
                660                 665                 670
Ile Val Gly Ser Asn Gly Ser Ser Arg Leu Gln Asp Ser Arg Ile
            675                 680                 685

(2) INFORMATION FOR SEQ ID NO:3:

(i) SEQUENCE CHARACTERISTICS:
        (A) LENGTH: 2169 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

GGGCCGGGGG CTGCAGCATG CTCTTGAGAT CTGTGGCCTG AAAGGCGCTG GAAGCAGAGC      60

CTGTGAGTGT GGTCCCCGTC ACCAGAGCCC CAACCCACCG CCGCCATGGT AGGAAAAGGT     120

GCCAAAGGGA TGCTGGTGAC GCTTCTCCCT GTTCAGAGAT CCTTCTTCCT GCCACCCTTT     180

TCTGGAGCCA CTCCCTCTAC TTCCCTAGCA GAGTCTGTCC TCAAAGTCTG GCATGGGGCC     240

TACAACTCTG GTCTCCTTCC CCAACTCATG GCCCAGCACT CCCTAGCCAT GGCCCAGAAT     300
```

-continued

```
GGTGCTGTGC CCAGCGAGGC CACCAAGAGG GACCAGAACC TCAAACGGGG CAACTGGGGC      360

AACCAGATCG AGTTTGTACT GACGAGCGTG GGCTATGCCG TGGGCCTGGG CAATGTCTGG      420

CGCTTCCCAT ACCTCTGCTA TCGCAACGGG GGAGGCGCCT TCATGTTCCC CTACTTCATC      480

ATGCTCATCT TCTGCGGGAT CCCCCTCTTC TTCATGGAGC TCTCCTTCGG CCAGTTTGCA      540

AGCCAGGGGT GCCTGGGGGT CTGGAGGATC AGCCCCATGT TCAAAGGAGT GGGCTATGGT      600

ATGATGGTGG TGTCCACCTA CATCGGCATC TACTACAATG TGGTCATCTG CATCGCCTTC      660

TACTACTTCT TCTCGTCCAT GACGCACGTG CTGCCCTGGG CCTACTGCAA TAACCCCTGG      720

AACACGCATG ACTGCGCCGG TGTACTGGAC GCCTCCAACC TCACCAATGG CTCTCGGCCA      780

GCCGCCTTGC CCAGCAACCT CTCCCACCTG CTCAACCACA GCCTCCAGAG GACCAGCCCC      840

AGCGAGGAGT ACTGGAGGCT GTACGTGCTG AAGCTGTCAG ATGACATTGG GAACTTTGGG      900

GAGGTGCGGC TGCCCCTCCT TGGCTGCCTC GGTGTCTCCT GGTTGGTCGT CTTCCTCTGC      960

CTCATCCGAG GGGTCAAGTC TTCAGGGAAA GTGGTGTACT TCACGGCCAC GTTCCCCTAC     1020

GTGGTGCTGA CCATTCTGTT TGTCCGCGGA GTGACCCTGG AGGGAGCCTT TGACGGCATC     1080

ATGTACTACC TAACCCCGCA GTGGGACAAG ATCCTGGAGG CCAAGGTGTG GGGTGATGCT     1140

GCCTCCCAGA TCTTCTACTC ACTGGCGTGC GCGTGGGGAG GCCTCATCAC CATGGCTTCC     1200

TACAACAAGT TCCACAATAA CTGTTACCGG GACAGTGTCA TCATCAGCAT CACCAACTGT     1260

GCCACCAGCG TCTATGCTGG CTTCGTCATC TTCTCCATCC TCGGCTTCAT GGCCAATCAC     1320

CTGGGCGTGG ATGTGTCCCG TGTGGCAGAC CACGGCCCTG GCCTGGCCTT CGTGGCTTAC     1380

CCCGAGGCCC TCACACTACT TCCCATCTCC CCGCTGTGGT CTCTGCTCTT CTTCTTCATG     1440

CTTATCCTGC TGGGGCTGGG CACTCAGTTC TGCCTCCTGG AGACGCTGGT CACAGCCATT     1500

GTGGATGAGG TGGGGAATGA GTGGATCCTG CAGAAAAAGA CCTATGTGAC CTTGGGCGTG     1560

GCTGTGGCTG GCTTCCTGCT GGGCATCCCC CTCACCAGCC AGGCAGGCAT CTATTGGCTG     1620

CTGCTGATGG ACAACTATGC GGCCAGCTTC TCCTTGGTGG TCATCTCCTG CATCATGTGT     1680

GTGGCCATCA TGTACATCTA CGGGCACCGG AACTACTTCC AGGACATCCA GATGATGCTG     1740

GGATTCCCAC CACCCCTCTT CTTTCAGATC TGCTGGCGCT TCGTCTCTCC CGCCATCATC     1800

TTCTTTATTC TAGTTTTCAC TGTGATCCAG TACCAGCCGA TCACCTACAA CCACTACCAG     1860

TACCCAGGCT GGGCCGTGGC CATTGGCTTC CTCATGGCTC TGTCCTCCGT CCTCTGCATC     1920

CCCCTCTACG CCATGTTCCG GCTCTGCCGC ACAGACGGGG ACACCCTCCT CCAGCGTTTG     1980

AAAAATGCCA CAAAGCCAAG CAGAGACTGG GGCCCTGCCC TCCTGGAGCA CCGGACAGGG     2040

CGCTACGCCC CCACCATAGC CCCCTCTCCT GAGGACGGCT TCGAGGTCCA GTCACTGCAC     2100

CCGGACAAGG CGCAGATCCC CATTGTGGGC AGTAATGGCT CCAGCCGCCT CCAGGACTCC     2160

CGGATATAG                                                             2169
```

GLYCINE TRANSPORTER

This application is a divisional of U.S. application Ser. No. 08/834,467, filed Apr. 11, 1997, now U.S. Pat. No. 6,008,015 which is incorporated by reference herein in its entirety.

This application is related to the following co-pending applications: "Glycine Transporter-Transfected Cells and Uses Thereof,", Ser. No. 08/655,836, filed May 31, 1996; "Pharmaceutical For Treatment Of Neurological And Neuropsychiatric Disorders," Ser. No. 08/656,063, filed May 31, 1996, and a Continuation-in-Part thereof, Ser. No. 08/808,754, filed Feb. 27, 1997; "Pharmaceutical For Treatment of Neuropsychiatric Disorders," and a Continuation-in-Part thereof, Ser. No. 08/808,755 filed Feb. 27, 1997, Ser. No. 08/655,912, filed May 31, 1996; "Pharmaceutical For Treating Of Neurological and Neuropsychiatric Disorders," Ser. No. 08/655,847, filed May 31, 1996, and a Continuation-in-Part thereof, Ser. No. 08/807,681, filed Feb. 27, 1997; and "Human Glycine Transporter," Attorney Docket No. 317743-108 Ser. No. 08/700,013, filed Aug. 20, 1996.

The present invention relates to nucleic acid encoding a "GlyT1d" member of the family of glycine transports, to the isolated protein encoded by the nucleic acid, and to the field of drug discovery.

Synaptic transmission is a complex for of intercellular communication that involves a considerable array of specialized structures in both the pre- and post-synaptic neuron. High-affinity neurotransmitter transports are one such component, located on the pre-synaptic terminal and surrounding glial cells (Kanner and Schuldiner, *CRC Critical Reviews in Biochemistry* 22: 1032, 1987). Transporters sequester neurotransmitter from the synapse, thereby regulating the concentration of neurotransmitter in the synapse, as well as its duration in the synapse therein, which together influence the magnitude of synaptic transmission. Further, by preventing the spread of transmitter to neighboring synapses, transporters maintain the fidelity of synaptic transmission. Last, by sequestering released transmitter into the presynaptic terminal, transports allow for transmitter reutilization.

Neurotransmitter transport is dependent on extracellular sodium and the voltage difference across the membrane; under conditions of intense firing, as, for example, during a seizure, transporters can function in reverse, releasing neurotransmitter in a calcium-independent non-exocytotic manner (Attwell et al., *Neuron* 11: 401–407, 1993). Pharmacologic modulation of neurotransmitter transports thus provides a means for modifying synaptic activity, which provides useful therapy for the treatment of neurological and psychiatric disturbances.

The amino acid glycine is a major neurotransmitter in the mammalian nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid, strychnine, and are thus referred to as "strychnine-sensitive." Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine functions in excitatory transmission by modulating the actions of glutamate, the major excitatory neurotransmitter in the central nervous system. See Johnson and Ascher, *Nature 325: 529–531, 1987*; Fletcher et al., *Glycine Transmission*, (Otterson and Storm-Mathisen, eds., 1990), pp. 193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that the neuron will fire an action potential. NMDA receptors are widely distributed throughout the brain, with a particularly high density in the cerebral cortex and hippocampal formation.

Molecular cloning has revealed the existence in mammalian brains of two classes of glycine transporters, termed GlyT1 and GlyT2. GlyT1 is found predominantly in the forebrain, and its distribution corresponds to that of glutamatergic pathways and NMDA receptors (Smith, et al., *Neuron* 8:927–935, 1992). Molecular cloning has further revealed the existence of three variants of GlyT-1, termed GlyT-1a, GlyT-1b and GlyT-1c (Kim et al., *Molecular Pharmacology* 45: 608–617, 1994), each of which displays a unique distribution in the brain and peripheral tissues. GlyT2, in contrast, is found predominantly in the brain stem and spinal cord, and its distribution corresponds closely to that of strychnine-sensitive glycine receptors (Liu et al., *J. Biol. Chem.* 268: 22802–22808, 1993; Jursky and Nelson, *J. Neurochem.* 64: 1026–1033, 1995. These observations are consistent with the view that, by regulating the synaptic levels of glycine, GlyT1 and GlyT2 selectively influence the activity of NMDA receptors and strychnine-sensitive glycine receptors, respectively.

Sequence comparisons of GlyT1 and GlyT2 have revealed that these glycine transporters are members of broader family of sodium-dependent neurotransmitter transporters, including, for example, transporters specific for gamma-amino-n-butyric acid (GABA) and others. Uhl, *Trends in Neuroscience* 15: 265–268, 1992: Clark and Amara, *BioEssays* 15: 323–332, 1993. Overall, each of these transporters includes 12 putative transmembrane domains that predominantly contain hydrophobic amino acids.

Compounds that inhibit or activate glycine transporters would be expected to alter receptor function, and provide therapeutic benefits in a variety of disease states. For example, inhibition of GlyT2 can be used to diminish the activity of neurons having strychnine-sensitive glycine receptors via increasing synaptic levels of glycine, thus diminishing the transmission of pain-related (i.e., nociceptive) information in the spinal cord, which has been shown to be mediated by these receptors. Yaksh, Pain, 111–123 (1989). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity, myoclonus, and epilepsy (Truong et al., *Movement Disorders*, 3, 77–87 (1988); Becker, *FASEB J.*, 4, 2767–2774 (1990)). Spasticity that can be treated via modulation of glycine receptors is associated with epilepsy, stroke, head trauma, multiple sclerosis, spinal cord injury, dystonia, and other conditions of illness and injury of the nervous system.

NMDA receptors are critically involved in memory and learning (Rison and Stanton, *Neurosci. Biobehav. Rev.*, 19, 533–552 (1995); Danysz et al., *Behavioral Pharmacol.*, 6, 455–474 (1995)); and, furthermore, decreased function of NMDA-mediated neurotransmission appears to underlie, or contribute to, the symptoms of schizophrenia (Olney and Farber, *Archives General Psychiatry* 52: 998–1007 (1996)). Thus, agents that inhibit Gly-T1 and thereby increase glycine activation of NMDA receptors can be used as novel antipsychotics and anti-dementia agents, and to treat other diseases in which cognitive processes are impaired, such as attention deficit disorders and organic brain syndromes. Conversely, over-activation of NMDA receptors has been implicated in a number of disease states, in particular the neuronal death associated with stroke and possibly neurodegenerative diseases, such as Alzheimer's disease, multi-infarct dementia, AIDS dementia, Parkinsons's disease, Huntington's disease, amyotrophic lateral sclerosis or other conditions in which neuronal cell death occurs, such as stroke and head trauma. Coyle & Puttfarcken, *Science* 262: 689–695, 1993; Lipton and Rosenberg, *New Engl. J. of Medicine,* 330: 613–622, 1993; Choi, *Neuron* 1: 623–634, 1988. Thus, pharmacological agents that increase the activity of GlyT-1 will result in decreased glycine-activation of NMDA receptors, which activity can be used to treat these, and related, disease states. Similarly, drugs that directly block the glycine site on the NMDA receptors can be used to treat these and related disease states.

SUMMARY OF THE INVENTION

The invention provides an isolated nucleic acid encoding a glycine transporter protein comprising a nucleic acid wherein:

(a) the encoded protein has a protein sequence of SEQ ID 2 or a protein sequence having at least about 99% sequence identity with SEQ ID 2; or (b) a glycine transporter protein-encoding portion of the nucleic acid has at least about 95% sequence identity with SEQ ID 1.

The invention further provides a cell comprising a nucleic acid encoding a glycine transporter, wherein the nucleic acid is functionally associated with a promoter, wherein:

(a) the encoded protein has a protein sequence of SEQ ID 2 or a protein sequence having at least about 99% sequence identity with SEQ ID 2; or (b) a protein-encoding portion of the nucleic acid has at least about 95% sequence identity with SEQ ID 1. A glycine transporter can be isolated from such a cell.

The invention further provides a method for characterizing a bioactive agent for treatment of a nervous system disorder or condition or for identifying bioactive agents for treatment of a nervous system disorder or condition, the method comprising (a) providing a first assay composition comprising (i) a cell according to the invention or (ii) an isolated glycine transporter protein comprising the amino acid sequence encoded by the nucleic acid, or the amino acid sequence resulting from cellular processing of the amino acid sequence encoded by the nucleic acid of the vector, (b) contacting the first assay composition with the bioactive agent or a prospective bioactive agent, and (c) measuring the amount of glycine transport exhibited by the assay composition.

Additionally, the invention provides a nucleic acid comprising an amplification primer or nuclease protection probe effective to identify GlyT1d and to distinguish GlyT1d from GlyT1a, GlyT1b, GlyT1c and GlyT2, which can be a vector comprising of the nucleic acid.

The invention further provides an isolated glycine transporter protein having a sequence of SEQ ID 2 or a sequence having at least about 99% sequence identity with SEQ ID 2, which can comprise isolated membranes in which the glycine transporter protein is an integral protein.

BRIEF DESCRIPTION OF THE DRAWINGS

FIG. 1 shows a cDNA sequence (SEQ ID 3) encompassing an open reading frame encoding GlyT1d (nucleotides 106–2169), and an aligned protein sequence (SEQ ID 2).

DEFINITIONS

Figure 2:
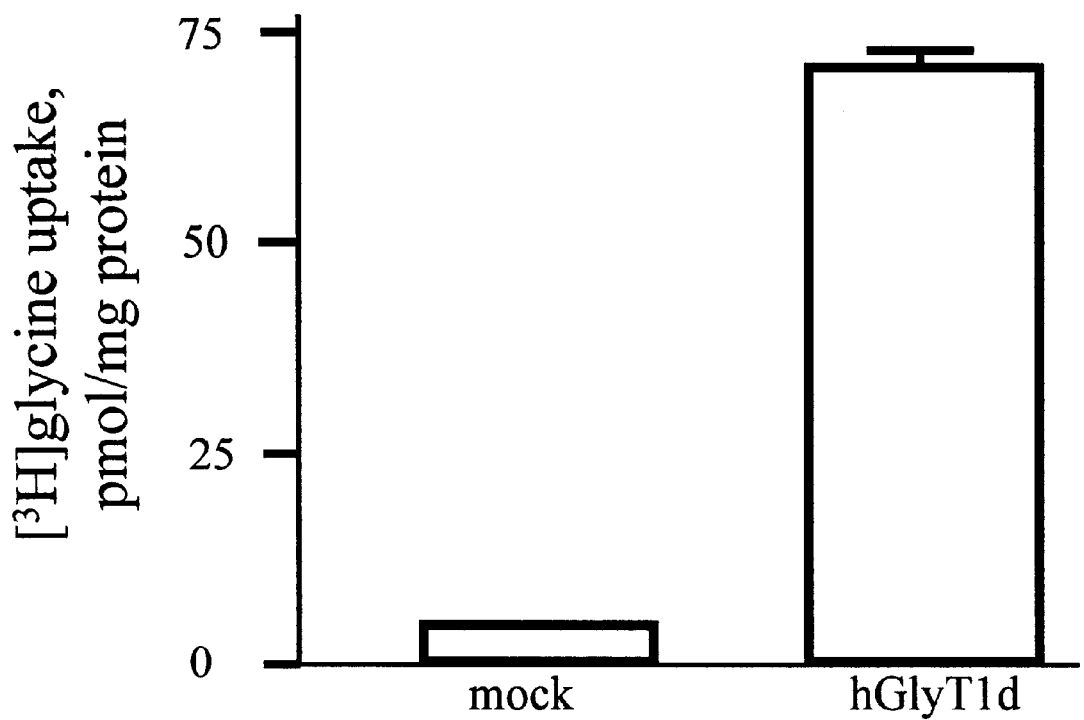
FIG. 2 shows glycine uptake in cells transfected with a GlyT1d expression vector.

For the purposes of this application, the following terms shall have the meaning set forth below.

Bioactive agent

A bioactive agent is a substance such as a chemical that can act on a cell, virus, tissue, organ or organism, including but not limited to drugs (i.e., pharmaceuticals) to create a change in the functioning of the cell, virus, organ or organism. Preferably, the organism is a mammal, more preferably a human. In a preferred embodiment of the invention, the method of identifying bioactive agents of the invention is applied to organic molecules having molecular weight of about 1500 or less.

Extrinsically-derived nucleic acid

Extrinsically-derived nucleic acids are nucleic acids that were introduced, through a recombinant technology, into a cell, a parent or ancestor of the cell, or a transgenic animal from which the cell is derived.

Extrinsic promoter functionally associated with a nucleic acid

An extrinsic promoter for a protein-encoding nucleic acid is a promoter distinct from that used in nature to express a nucleic acid for that protein. A promoter is functionally associated with the nucleic acid if in a cell that is compatible with the promoter the promoter can act to allow the transcription of the nucleic acid.

Nucleic acid-specific property

Nucleic acid-specific properties are properties that can be used to distinguish differing nucleic acid molecules. Such properties include, without limitation (i) the nucleotide sequence of all or a portion of the molecule, (ii) the size of the molecule, for instance as determined by electrophoresis, (iii) the fragmentation pattern generated by (a) treatment with chemicals that fragment nucleic acid, or (b) nucleases, and (iv) the ability of the molecule or fragments thereof to hybridize with defined nucleic acid probes.

Prospective agent

Prospective agents are substances which are being tested by the screening method of the invention to determine if they affect glycine transport.

Sequence identity

"Identity," as known in the art, is a relationship between two or more polypeptide sequences or two or more polynucleotide sequences, as determined by comparing the sequences, particularly, as determined by the match between strings of such sequences. "Identity" is readily calculated by known methods (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H.

G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two sequences, the term is well known to skilled artisans (see, for example, *Sequence Analysis in Molecular Biology; Sequence Analysis Primer*; and Carillo, H., and Lipman, D., SIAM *J. Applied Math.*, 48: 1073 (1988)). Methods commonly employed to determine identity between sequences include, but are not limited to those disclosed in Carillo, H., and Lipman, D., SIAM *J. Applied Math.*, 48: 1073 (1988) or, preferably, in Needleman and Wunsch, *J. Mol. Biol.*, 48: 443–445, 1970, wherein the parameters are as set in version 2 of DNASIS (Hitachi Software Engineering Co., San Bruno, Calif.). Computer programs for determining identity are publicly available. Preferred computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990)). The BLAST X program is publicly available from NCBI (blast@ncbi.nlm.nih.gov) and other sources (*BLAST Manual*, Altschul, S., et al., NCBI NLM NIH Bethesda, Md. 20894; Altschul, S., et al., *J. Mol. Biol.* 215: 403–410 (1990)).

DETAILED DESCRIPTION

The GlyT1d nucleic acid sequence of SEQ ID 1 or the corresponding encoded protein sequence of SEQ ID 2, reflect a type of glycine transporter previously unrecognized despite ample work in the field reflected by the GlyT1 sequence reports recited below:

| human GlyT1a | GenBank No. | Kim et al., Molec. Pharmacol. 45: 608–617. 1994. |
| human GlyT1b | GenBank No. | |
| human GlyT1c | GenBank No. | |
| rat GlyT1a | GenBank No. | Borowsky et al., Neuron 10: 851–863, 1993; Guastella et al., Proc. Natl. Acad. Sci. USA 89: 7189–7193, 1992. |
| rat GlyT1b | GenBank No. | Smith et al., Neuron 8: 927–935, 1992. |

Nucleic Acid-encoding glycine transporter

To construct non-naturally occurring glycine transporter-encoding nucleic acids, the native sequences can be used as a starting point and modified to suit particular needs. For instance, the sequences can be mutated to incorporate useful restriction sites. See Maniatis et al. *Molecular Cloning, a Laboratory Manual* (Cold Spring Harbor Press, 1989). Such restriction sites can be used to create "cassettes", or regions of nucleic acid sequence that are facilely substituted using restriction enzymes and ligation reactions. The cassettes can be used to substitute synthetic sequences encoding mutated glycine transporter amino acid sequences. Alternatively, the glycine transporter-encoding sequence can be substantially or fully synthetic. See, for example, Goeddel et al., *Proc. Natl. Acad. Sci. USA*, 76: 106–1160, 1979. For recombinant expression purposes, codon usage preferences for the organism in which such a nucleic acid is to be expressed are advantageously considered in designing a synthetic glycine transporter-encoding nucleic acid. For example, a nucleic acid sequence incorporating prokaryotic codon preferences can be designed from a mammalian-derived sequence using a software program such as Oligo-4, available from National Biosciences, Inc. (Plymouth, Minn.).

The nucleic acid sequence embodiments of the invention are preferably doxyribonucleic acid sequences, preferably double-stranded deoxyribonucleic acid sequences. However, they can also be ribonucleic acid sequences, or nucleic acid mimics, meaning compounds designed to preserve the hydrogen bonding and base-pairing properties of nucleic acid, but which differ from natural nucleic acid in, for example, susceptibility to nucleases.

Numerous methods are known to delete sequence from or mutate nucleic acid sequences that encode a protein and to confirm the function of the proteins encoded by these deleted or mutated sequences. Accordingly, the invention also relates to a mutated or deleted version of a nucleic acid sequence that encodes a protein that retains the ability to bind specifically to glycine and to transport glycine across a membrane. These analogs can have N-terminal, C-terminal or internal deletions or substitutions, so long as glycine transporter function is retained. The remaining GlyT1d protein sequence will preferably have no more than about 4 amino acid variations, preferably no more than 2 amino acid variations, more preferably no more than 1 amino acid variation, relative to the protein sequence of SEQ ID 2. the point variations are preferably conservative point variations. Preferably, the protein analogs will have at least about 99% sequence identity, preferably at least about 99.5%, more preferably at least about 99.8%, still more preferably at least about 99.9%, to the protein sequence of SEQ ID 2.

Mutational and deletional approaches can be applied to all of the nucleic acid sequences of the invention that express GlyT1d proteins. As discussed above, conservative mutations are preferred. Such conservative mutations include mutations that switch one amino acid for another within one of the following groups:

1. Small aliphatic, nonpolar or slightly polar residues: Ala, Ser, Thr, Pro and Gly;

2. Polar, negatively charged residues and their amides: Asp, Asn, Glu and Gln;

3. Polar, positively charged residues: His, Arg and Lys;

4. Large aliphatic, nonpolar residues: Met, Leu, Ile, Val and Cys; and

5. Aromatic residues: Phe, Tyr and Trp.

A preferred listing of conservative variations is the following:

| Original Residue | Variation |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Try | Trp, Phe |
| Val | Ile, Leu |

The types of variations selected may be based on the analysis of the frequencies of amino acid variations between homologous proteins of different species developed by Schulz et al., *Principles of Protein Structure*, Springer-Verlag, 1978, on the analyses of structure-forming potentials developed by Chou and Fasman, *Biochemistry* 13: 211, 1974 and *Adv. Enzymol.*, 47: 45–149, 1978, and on the analysis of hydrophobicity patterns in proteins developed by Eisenberg et al., *Proc. Natl. Acad. Sci. USA* 81: 140–144, 1984; Kyte & Doolittle; *J. Molec. Biol.* 157: 105–132, 1981, and Goldman et al., *Ann. Rev. Biophys. Chem.* 15: 321–353, 1986. all of the references of this paragraph are incorporated herein in their entirety by reference.

The nucleic acids of the invention preferably have at least about 95% sequence identity with SEQ ID 1, more preferably at least about 97% or at least about 98% sequence identity.

For the purposes of this application, a nucleic acid or protein of the invention is "isolated" if it has been separated from other molecules or macromolecules of the cell or tissue from which it is derived. Preferably, the composition containing the nucleic acid is at least about 10-fold enriched, with respect to nucleic acid content, over the composition of the source cells. Preferably, the nucleic acid is substantially pure, meaning purity of at least about 60% w/w with respect to other nucleic acids, more preferably at least about 80%, still more preferably at least about 90%, yet more preferably at least about 95%.

Nuclease Protection Probes

The invention also provides nuclease protection probes. Generally, these probes include sequence from SEQ ID 3, or a homolog from another species, encompassing nucleotides corresponding to nucleotides 1 and 297 of SEQ ID 3, and sufficient sequence to each side of the bases to allow for the specific identification of GlyT1d mRNA. The invention further provides a method comprising determining whether a tissue expresses Gly1d by applying a nuclease protection assay. Nuclease protection assays are described for example in Ausubel et al., *Current Protocols in Molecular Biology*, John Wiley & Sons, New York, and in the kits sold by Ambion (Austin, Tex.).

Without limitations, examples of the uses for hybridization probes in nuclease protection assays include: measuring mRNA levels, for instance to identify a sample's tissue type or to identify cells that express abnormal levels of glycine transporter; and detecting polymorphisms in the glycine transporter gene. RNA hybridization procedures and protection assay methods are described, for example, in Maniatis et al. *Molecular Cloning, a Laboratory Manual* (Cold Spring Harbor Press, 1989).

Amplification Primers

Rules for designing polymerase chain reaction ("PCR") primers are now established, as reviewed by *PCR Protocols*, Cold Spring Harbor Press, 1991. Degenerate primers, i.e., preparations of primers that are heterogeneous at given sequence locations, can be designed to amplify nucleic acid sequences that are highly homologous to, but not identical to, a GlyT1 nucleic acid. Strategies are now available that allow for only one of the primers to be required to specifically hybridize with a known sequence. See, Froman et al., *Proc. Natl. Acad. Sci. USA* 85: 8998, 1988 and Loh et al., *Science* 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods of amplifying nucleic acid generally utilize at least two primers. One of these primers is capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, *PCR Protocols*, Cold Spring Harbor Press, 1991.

Other amplification procedures are available that utilize oligonucleotides to direct the specificity of the amplification, such as the ligase chain reaction (LCR), strand displacement amplification (SDA; see, for example, Walker et al., *PCR Methods and Applications* 3: 1–6, 1993), nucleic acid sequence-based amplification (NASBA; see, for example, Gemen et al., *J. Virol. Methods* 43: 177–188, 1993), and transcription-mediated amplification (TMA; see, for example, Pfyffer et al., *J. Clin. Micro.* 34: 834–841, 1996). LCR uses the source nucleic acid as a template to bring two probe oligonucleotides close to one another to allow ligation with or without provision for polymerization to fill in relatively small gaps between the probes). Upon ligation, the two linked probes provide additional template for the next cycle of the reaction. As with PCR, approaches can be devised to use a single probe corresponding to the source nucleic acid. The present invention also encompasses oligonucleotides designed to specifically identify GlyT1d.

Vectors

A suitable expression vector is capable of ostering expression of the included GlyT1d encoding DNA in a host cell, which can be eukaryotic, fungal, or prokaryotic. Suitable expression vectors include pRc/CMV (Invitrogen, San Diego, Calif.), pRc/RSV (Invitrogen), pcDNA3 (Invitrogen), Zap Express Vector (Stratagene Cloning Systems, LaJolla, Calif.), pBk/CMV or pBk-RSV vectors (Stratagene), Bluescript 11 SK+/– Phagemid Vectors (Stratagene), LacSwitch (Stratagene), pMAM and pMAM neo (Clontech, Palo Alto, Calif.), pKSV10 (Pharmacia, Piscataway, N.J.), pCRscript (Stratagene) and pCR2.1 (Invitrogen), among others. Useful yeast expression systems include, for example, pYEUra3 (Clontech). Useful baculovirus vectors include several viral vectors from Invitrogen (San Diego, Calif.) such as pVL1393, pVL1392, pBluBac2, pBluBacHis A, B or C, and pbacPAC6 (from Clontech). In one embodiment, the expression vector is an inducible expression vector. Typically, for this inducible embodiment, transformed cells are grown in the absence of the induction condition until such time as protein expression is desired.

Cells

In one embodiment of the invention, the transporter is preferably expressed in a mammalian cell line, preferably a transformed cell line with an established cell culture history. In this embodiment, particularly preferred cell lines include COS-1, COS-7, LM(tk⁻), HeLa, HEK293, CHO, Rat-1 and NIH3T3. Other preferred cells include avian cells such as QT-6 cells. Other cells that can be used include insect cells such as drosophila cells, fish cells, amphibian cells and reptilian cells.

In another embodiment, the transporter is expressed in a cell line that is more inexpensively maintained and grown than are mammalian or avian cell lines, such as a bacterial cell line or a yeast cell line.

Isolated Glycine Transporter

The invention also provides for the GlyT1d proteins encoded by any of the nucleic acids of the invention preferably in a purity achieved, for example, by applying protein purification methods, such as those described below, to a lysate of a recombinant cell according to the invention.

The GlyT1d variants of the above paragraphs can be used to create organisms or cells that have GlyT1d activity. Purification methods, including associated molecular biology methods, are described below.

Method of Producing Glycine Transporter

One simplified method of isolating polypeptides synthesized by an organism under the direction of one of the nucleic acids of the invention is to recombinantly express a fusion protein wherein the fusion partner is facilely affinity purified. For instance, the fusion partner can be glutathione S-transferase which is encoded on commercial expression vectors (e.g., vector pGEX4T3, available from Pharmcia, Piscataway, N.J.). The fusion protein can then be purified on a glutathione affinity column (for instance, that available from Pharmacia, Piscataway, N.J.). Of course, the recombinant polypeptides can be affinity purified without such a fusion partner using an appropriate antibody that binds to GlyT1d. Methods of producing such antibodies are available to those of ordinary skill in light of the ample description herein of GlyT1d expression systems and known antibody production methods. See, for example, Ausubel et al., *Short Protocols in Molecular Biology*, John Wiley & Sons, New York, 1992. If fusion proteins are used, the fusion partner can be removed by partial proteolytic digestion approaches that preferentially attack unstructured regions such as the linkers between the fusion partner and GlyT1d. The liners can be designed to lack structure, for instance using the rules for secondary structure forming potential developed, for instance, by Chou and Fasman, *Biochemistry* 13: 211, 1974 and Chou and Fasman, *Adv. in Enzymol.* 47: 45–147, 1978. The linker can also be designed ti incorporate protease target amino acids, such as, arginine and lysine residues, the amino acids that define the sites cleaved by trypsin. To create the linkers, standard synthetic approaches for making oligonucleotides can be employed together with standard subcloning methodologies. Other fusion partners besides GST can be used. Procedures that utilize eukaryotic cells, particularly mammalian cells, are preferred since these cells will post-translationally modify the protein to create molecules highly similar to or functionally identical to native proteins.

Additional purification techniques can be applied, including without limitation, preparative electrophoresis, FPLC (Pharmacia, Uppsala, Sweden), HPLC (e.g., using gel filtration, reverse-phase or mildly hydrophobic columns), gel filtration, differential precipitation (for instance, "salting out" precipitations), ion-exchange chromatography and affinity chromatography.

Because GlyT1d is a membrane protein, which by analogy to related transporter proteins is believed to have twelve transmembrane sequences, isolation methods will often utilize detergents, generally non-ionic detergents, to maintain the appropriate secondary and tertiary structure of the protein. See, for example, Lopez-Corcuera et al., *J. Biol. Chem.* 266: 24809–24814, 1991. For a description of methods for re-integrating a solubilized transporter into a membrane, see Lopez-Corcuera et al., *J. Biol. Chem.* 266: 24809–24814, 1991. Other re-integration methods are described, for example, in: Montel, "Functional Reconstitution of Membrane Proteins in Planar Lipid Bilayer Membranes," in *Techniques of the Analysis of Membrane Proteins* (Ragan and Cherry, eds.), London, Chapman & Hall, pp. 97–128, 1986; Silvius, *Annu. Rev. Biophys. Biomol. Struct.* 21: 323–348, 1992; Madden, *Chem. Phys. Lipids* 40: 207–222, 1986. It will be understood that a preferred form of the protein is integral to a lipid bilayer, meaning that at least some detergent is generally required to dislodge the protein from the membrane. Integral proteins typically have at least one domain that extends away from the lipid bilayer.

The isolation of GlyT1d can comprise isolating membranes from cells that have been transformed to express GlyT1d. Preferably, such cells express GlyT1d in sufficient copy number such that the amount of GlyT1d in a membrane fraction is at least about 10-fold higher than that found in comparable membranes from cells that naturally express GlyT1d, more preferably the amount is at least about 100-fold higher. If needed, specific membrane fractions, such as a plasma membrane fraction, can be isolated.

Preferably, the protein is substantially pure, meaning a purity of at least 60% w/w with respect to other proteins. For the purposes of this application, GlyT1d is "isolated" if it has been separated from other proteins or other macromolecules of the cell or tissue from which it is derived. Preferably, the composition containing GlyT1d is at least about 10-fold enriched, preferably at least about 100-fold, with respect to protein content, over the composition of the source cells.

Expression of GlyT1d by RNA Insertion

It will be recognized that GlyT1d can be expressed by the simple method of inserting mRNA into a cell. RNA for these uses can be prepared by sub-cloning the nucleic acid encoding a protein with GlyT1d activity into a vector containing a promoter for high efficiency in vitro transcription, such as a SP6 or T7 RNA polymerase promoter. RNA production from the vector can be conducted, for instance, with the method described in Ausubel et al., *Short Protocols in Molecular Biology*, John Wiley & Sons, New York, 1992, pp. 10–63 to 10–65. Insertion of RNA into Xenopus-derived oocytes is described, for instance, in Liu et al. *FEBS Letters* 305: 110–114, 1992 and Bannon et al., *J. Neurochem.* 54: 706–708, 1990.

Alternatively, it will be recognized that GlyT1d can be expressed by the simple method of inserting mRNA into an in vitro translation system, which can be a membrane-containing translation system. Expression of proteins in vitro is described, for instance, in Ausubel et al., *Short Protocols in Molecular Biology*, John Wiley & Sons, New York, 1992, pp. 10-63 to 10-65. See, also, Guastella et al., *Science* 249: 1303–1306, 1990 (in vitro expression of a transporter). The use of subcellular membranous material to produce membrane proteins in vitro is described in Walter and Blobel, *Meth. Enzymol.* 96: 84, 1983 (for rabbit reticulocyte translation system) and Spiess and Lodish, *Cell* 44: 177, 1986 (for wheat germ translation system).

Method of Characterizing or Identifying agent

A method for the analysis of or screening for a bioactive agent for treatment of a disease or condition associated with a nervous system disorder to condition comprises, for example, culturing separately first and second cells, wherein the first and second cells are preferably of the same species, more preferably of the same strain thereof, and comprise an exogenous nucleic acid encoding a glycine transporter as described herein. The disorders or conditions for which the agent can be used for treatment include, but are not limited to, disorders or conditions such as pain, myoclonus, muscle spasm, muscle hyperactivity, epilepsy, spasticity, stroke, head trauma, neuronal cell death, multiple sclerosis, spinal cord injury, dystonia, Huntington's disease or amyotrophic lateral sclerosis, cognitive or memory disorders, Alzheimer's disease, attention deficit disorders, organic brain syndromes, and schizophrenia. These agents can function through one of the GlyT1 or GlyT2 transports, or via a receptor. Even where the primary pharmacologic mechanism of a compound is not the GlyT1d transporter, the characterization of the compound's activity at the GlyT1d transporter is important to more fully characterize the pharmacology of the compound during the drug discovery process. In the method of the invention, a first cell is contacted with the bioactive agent or a prospective agent, which is preferably a compound, such as a peptide or an organic compound in the presence of glycine. The contacted first cell is then tested for enhancement or inhibition of glycine transport into the first cell as compared to glycine transport into the second cell that was not contacted with the compound (i.e., the control cell). Such analysis or screening preferably includes activities of finding, learning, discovering, determining, identifying, or ascertaining.

Alternatively, the assay can utilize a composition comprising an isolated GlyT1d transporter in place of cells. Preferably, such preparation of isolated transporter will comprise vesicles of membrane or lipid bilayer, which vesicles have an inside and an outside across which transport can be measured. See, for example, Kanner, *Biochemistry* 17: 1207–1211, 1978.

A bioactive agent is an enhancer of glycine transport uptake if at the end of the test the amount of intracellular or intravesicle glycine is greater in the agent-contacted composition than in the non-agent-contacted composition; conversely, a bioactive agent is an inhibitor of glycine transport if the amount of intracellular or intravesicle glycine is greater in the non-agent-contacted composition as compared to the other. Preferably, the difference in glycine uptake between a tested first composition and a control second composition is at least about two-fold; more preferably, the difference is at least about five-fold; most preferably, the difference is at least about ten-fold or greater.

A bioactive agent that is an inhibitor or an enhancer with respect to the GlyT1d transporter may have a neutral or opposite effect with another glycine transporter, such as another of the GlyT1 transporters. Preferred bioactive agents have specificity to enhance or inhibit the GlyT1d transporter and have neutral or negligible effect on other glycine transports. In particular, preferred bioactive agents have a neutral or negligible effect on the GlyT1b, GlyT1c and GlyT2 transporters. In another preferred embodiment, bioactive agents have a neutral or negligible effect on the GlyT1a transporter. Preferably, a bioactive agent has at least an order of magnitude greater potency, reflected in a concentration dependent parameter such as the $IC_{50}$ value, in inhibiting or activating glycine uptake mediated by the GlyT1d transporter as compared to its effect on the second glycine transporter. More preferred agents have greater potencies of at least about 100-fold for one of the glycine transporters as compared to the other.

The bioactive agent can be any compound, material, composition, mixture, or chemical, that can be presented to a glycine transporter in a form that allows for the agent to diffuse so as to contact the transporter. Such bioactive agents include but are not limited to polypeptides preferably of about two up to about 25 amino acids in length, more preferably from about two to about ten, yet more preferably from about two to about five amino acids in length. Other suitable bioactive agents in the context of the present invention include small organic compounds, preferably of molecular weight between about 100 daltons and about 5,000 daltons, and are composed of such functionalities as alkyl, aryl, alkene, alkyne, halo, cyano and other groups, including heteroatoms or not. Such organic compounds can be carbohydrates, including simple sugars, amino or imino acids, nucleic acids, steroids, and others. The chemicals tested as prospective agents can be prepared using combinatorial chemical processes known in the art or conventional means for chemical synthesis. Preferably, bioactive agents are useful as drugs for treatment of nervous system disorders or conditions.

Some compounds that inhibit GlyT1 or GlyT2 mediated transport also bind to the glycine binding site on the strychnine-sensitive receptor, or to the glycine binding site on the NMDA receptor. Such binding to the strychnine-sensitive receptor can be identified by a binding assay whereby, for example, radiolabeled strychnine is placed in contact with a preparation of strychnine-sensitive receptors, such as can be prepared from a membrane fraction from spinal cord or brain stem tissue. A membrane fraction can be prepared using conventional means, including, for example, methods of homogenization and centrifugation.

Such binding to the NMDA receptor can be identified by a binding assay whereby, for example, radiolabeled glycine or D-serine (which is believed to also be an agonist of this receptor) is placed in contact with a preparation of NMDA receptors, such as can be prepared from a membrane fraction from neuronal cells or brain tissue. Grimwood et al., *Molec. Pharmacol.*, 41: 923–930, 1992. The NMDA receptors located in such membranes are treated using mild detergent, such as about 0.1% to about 0.5% saponin, to remove any endogenous glycine, D-serine or glutamate.

The ligand used in such a binding assay is radiolabeled with an detectable isotope, such as radioactive isotopes of carbon or hydrogen. Specific binding of the radiolabeled ligand is then determined by subtracting the radioactivity due to non-specific binding from that which is due to total (i.e., specific and non-specific) binding of the radiolabeled ligand. The radioactivity due to non-specific binding is determined by measuring the amount of radiolabel associated with a strychnine-sensitive or NMDA receptor-containing membrane fraction that has been contacted with both radiolabeled ligand and a significant excess of non-radiolabeled ligand, such as a 100-fold excess. The radioactivity due to total binding of the radiolabeled ligand is determined by measuring the amount of radiolabel bound to the receptor preparation in the absence of non-radiolabeled ligand. For the NMDA receptor, one can also measure binding to the glycine site on the receptor using labeled analogs of amino acids, such as, for example, dichlorokynurenic acid or L-689,560. See, for example, Grimwood et al., *Molecular Pharmacol.*, 49: 923–930, 1992.

Another way to measure binding of a compound to the glycine site on the NMDA receptor is by measuring the compound's ability to modulate the binding of [$^3$H]MK-801 to the NMDA receptor. MK-801 binds to the NMDA receptor at a different site than does glycine, but binding of glycine or other ligands to the glycine site can allosterically modulate the binding of MK-801. an advantage of this technique is that it allows one to distinguish compounds having agonist activity from those having antagonist activity at the NMDA-receptor-glycine binding site. In particular, compounds having agonist activity in this assay enhance MK-801 binding; conversely, compounds having antagonist activity inhibit MK-801 binding. Serner and Calligaro, *Soc. Neurosci. Abstr.*, 21, 351 (1995); Calligaro et al., *J. Neurochem.*, 60, 2297–2303 (1993).

Functional ion-flux assays are used to measure the effect of compounds identified by the present invention in enhancing or inhibiting calcium flux (for NMDA receptor preparations) or chloride flux (for strychnine-sensitive receptor preparations). This test is performed on cell cultures that have membrane-bound NMDA receptors or strychnine-sensitive receptors and glycine transporters. Such cells include neuronal cells generally, including those of the brain stem and spinal cord, and cell lines derived therefrom, and any other cell that has been induced or transfected to express NMDA receptors or strychnine-sensitive receptors. Calcium used in such a test is commonly the $^{45}$Ca isotope, although other calcium measuring techniques can be used as well, such as calcium-associated fluorescence, which can be fluorescence associated with a calcium chelator, and the like. Chloride used in such a test usually includes the isotope $^{36}$Cl. By whatever method the calcium or chloride is monitored, ion flux can be enhanced or inhibited as a result of the discrete addition of a bioactive agent of the present invention. An advantage of this system is that it allows one to monitor the net effect on NMDA receptor or strychnine-sensitive receptor function of a compound that interacts with both the glycine site on a receptor and on a glycine transporter.

GlyT-1 inhibitors that are also NMDA receptor agonists act to alleviate schizophrenia and enhance cognition both by increasing glycine concentrations at the NMDA receptor-expressing synapses via inhibition of the glycine transporter, and via directly enhancing NMDA receptor activity. Glycine transporter inhibitors that are also NMDA receptor antagonists can nonetheless retain activity in schizophrenia and enhancing cognition, if the increase in glycine due to glycine transport inhibition prevails over the NMDA antagonism. Where the NMDA receptor antagonist activity prevails over the effect of increased extracellular glycine resulting from inhibition of the glycine transporter, these compounds are useful, for example, in limiting the cell damage and cell death arising after stroke or as a consequence of neurodegenerative diseases such as Alzheimer's, Parkinson's, AIDS dementia, Huntington's, and the like. See, for example, Choi, supra; Coyle and Puttfarcken, supra; Lipton and Rosenberg, supra; Brennan, *Chem. Eng. News* (May 13, 1996), pp. 41–47; Leeson, *in Drug Design For Neuroscience* (Alan P. Kozikowski, ed., 1993), pp. 339–383.

GlyT2 inhibitors that are also strychnine-sensitive receptor agonists act in the above-described indications by increasing glycine concentrations at the strychnine-sensitive receptor-expressing synapses via inhibition of the glycine transporter, and via directly enhancing strychnine-sensitive receptor activity. Glycine transporter inhibitors that are also strychnine-sensitive receptor antagonists can nonetheless retain activity in treating these indications, if the increase in glycine due to glycine transport inhibition prevails over the strychnine-sensitive receptor antagonism. Where the strychnine-sensitive receptor antagonist activity prevails over the effect of increased extracellular glycine resulting from inhibition of the glycine transporter, these compounds are useful, for example, in treating conditions associated with decreased muscle activity such as myasthenia gravis.

As discussed above, the bioactive agents of the invention can have a number of pharmacological actions. The relative effectiveness of the compounds can be assessed in a number of ways, including the following:

1. Comparing the activity mediated through GlyT1 and GlyT2 transporters. This testing identifies bioactive agents (a) that are more active against GlyT1 transporters and thus more useful, for example, in treating or preventing schizophrenia, increasing cognition and enhancing memory or (b) that are more active against GlyT2 transporters and thus more useful, for example, in treating or preventing epilepsy, pain or spasticity.

2. Testing for strychnine-sensitive receptor or NMDA receptor binding. This test establishes whether there is sufficient binding at this site to warrant further examination of the pharmacological effect of such binding.

3. Testing the activity of the compounds in enhancing or diminishing ion fluxes in primary tissue culture, for example chloride ion fluxes mediated by strychnine-sensitive receptors or calcium ion fluxes mediated by NMDA receptors. A bioactive agent that increases in flux either (a) has little or no antagonist activity at the strychnine-sensitive receptor and should not affect the potentiation of glycine activity through GlyT1 or GlyT2 transporter inhibition or (b), if marked increases are observed over results with comparative GlyT1 or GlyT2 inhibitors (which have little direct interaction with NMDA or strychnine-sensitive receptors, respectively), then the agent is a receptor agonist.

The agent analysis method of the invention can be used to characterize whether a bioactive agent is useful in treating an indication in which NMDA receptors and GlyT1 transporters are implicated. In this case, generally, a lower measure of activity with respect to strychnine-sensitive receptors and GlyT2 transporters is more desirable. Alternatively, the agent analysis method of the invention can be used to characterize whether a bioactive agent is useful in treating an indication in which strychnine-sensitive receptors and GlyT2 transporters are implicated. In this case, generally, a lower measure of activity with respect to NMDA receptors and GlyT1 transporters is more desirable.

The following examples further illustrate the present invention, but of course, should not be construed as in any way limiting its scope.

EXAMPLE 1

GlyT1d Cloning

The cDNA encoding the 5' end of human GlyT1d was generated by reverse-transcription PCR (RT-PCR) in one step. A primer corresponding to the human GlyT1c sequence from +553 to +534 (5' CCACATTGTAGTAGATGCCG 3') was used to prime cDNA synthesis from human spinal cord poly A mRNA (Clontech, Palo Alto, Calif.). The following primer pair was then used in a PCR reaction:

```
Primer 1:    5' GGGCCGGGGGCTGCAGCATGC 3'
Primer 2:    5' CAGCACCATTCTGGGCCATGGC 3'
```

The 307 bp fragment generated by primers 1 and 2 was cloned into pCR2.1 (Invitrogen, San Diego, Calif.). The resulting clone (pCRh1d-2) was sequenced using the Auto-Read sequencing kit (Pharmacia, Piscataway, N.J.), and found to include sequence (nucleotides 1–307 of SEQ ID 3) related to human GlyT1a and GlyT1c.

EXAMPLE 2

Full Length Human Glyt1d

The pCRh1d-2 clone described above and a full length GlyT1c expression clone (hGlyT1c/RSV) were used to construct a full length GlyT1d coding sequence. The pCRh1d-2 plasmid was digested with NcoI, filled-in (i.e., blunt-ended) using the Klenow fragment of DNA polymerase, and digested with PflMI. A resulting 169 bp fragment corresponded to nts 105 to 267 of pCRh1d-2 contained the peptide-encoding portion of exon 1a and a portion of human GlyT1c. To complete the portion encoding 3' sequence, hGlyT1c/RSV was digested with XbaI and partially digested with PflMI to generate a 1.9 kb fragment corresponding to +175 to +2103 of human GlyT1c. Finally, the NcoI (filled)-PflMI fragment of pCRh1d and the pFlMI-XbaI were cloned into a pcDNA3 vector (Invitrogen) digested with EcoRV and XbaI. The expression clone phG1d/CMV thus obtained includes the sequence of human GlyT1d from 105 to 2193 (of SEQ ID 3) under the control of a human cytomegalovirus (CMV) promoter.

EXAMPLE 3

Confirmation of In Vivo utilization of GlyT1d

GlyT1d mRNA was detected in RNA isolated from human tissue by RNAse Protection Assay. The pCRh1d-2 plasmid described above, which contained a region unique to GlyT1d, was used to generate a probe for RNAse protection. After digestion of the plasmid with BgII, T7 polymerase was used to transcribe a 333 nucleotide antisense probe, which contained 278 nucleotides of sequence specific for GlyT1d, and included 55 nucleotides from the pCR2.1 vector. Hybridization of this probe to RNA isolated from human adrenal gland, uterus, total brain, hipocampus, corpus callosum, substantia nigra, cerebellum and spinal cord, followed by RNAse digestion (according to the instructions in the RPA II RNase protection kit, Ambion, Austin Tex.), produced a protected fragment with the predicted size of 278 nucleotides, verifying the presence of GlyT1d mRNA in all of these human tissues.

EXAMPLE 4

Transfection

This example sets forth methods and material used for growing and transfecting QT-6 cells, which are avian fibroblasts derived from quail. Transfections with pHGT2 have been conducted, as have transfections with GlyT1 vectors, though these latter transfections were conducted at separate times.

QT-6 cells were obtained from American Type Culture Collection (Accession No. ATCC CRL-1708). Complete QT-6 medium for growing QT-6 was Medium 199 (Sigma Chemical Company, St. Louis, Mo.; hereinafter "Sigma") supplemented to be 10% tryptose phosphate; 5% fetal bovine serum (Sigma); 1% penicillin-streptomycin (Sigma); and 1% sterile dimethylsulfoxide (DMSO; Sigma). Other solutions required for growing or transfecting QT-6 cells included:

DNA/DEAE Mix: 450 µl TBS, 450 µl DEAE Dextran (Sigma), and 100 µl of DNA (4 µg) in TE, where the DNA included GlyT1a, GlyT1b, GlyT1c, GlyT1d or GlyT2 encoding DNA, in a suitable expression vector. The DNA plasmids for expressing the glycine transporters were as defined below.

PBS: Standard phosphate buffered saline, pH 7.4 including 1 mM $CaCl_2$ and 1 mM $MgCl_2$ sterilized through a 0.2 µm filter.

TBS: One ml of Solution B, 10 ml of Solution A; brought to 100 ml with distilled $H_2O$; filter-sterilized and stored at 4° C.

RE: 0.01M Tris, 0.001M EDTA, pH 8.0.

DEAE dextran: Sigma, #D-9885. A stock solution was prepared consisting of 0.1% (1 mg/ml) of the DEAE dextran in TBS. The stock solution was filter sterilized and frozen in 1 ml aliquots.

Chloroquine: Sigma, #C-6628. A stock solution was prepared consisting of 100 mM chloroquine in $H_2O$. The stock solution was filter-sterilized and stored in 0.5 ml aliquots, frozen.

| Solution A (10X): | |
|---|---|
| NaCl | 8.00 g |
| KCl | 0.38 g |
| $Na_2HPO_4$ | 0.20 g |
| Tris base | 3.00 g |

The solution was adjusted to pH 7.5 with HCl, brought to 100.0 ml with distilled $H_2O$, and filter-sterilized and stored at room temperature.

| Solution B (100X): | |
|---|---|
| $CaCl_2$ $2H_2O$ | 1.5 g |
| $MgCl_2$ $6H_2O$ | 1.0 g |

The solution was brought to 100 ml with distilled $H_2O$, and filter-sterilized; the solution was then stored at room temperature.

HBSS: 150 mM NaCl, 20 mM HEPES, 1 mM $CaCl_2$, 10 mM glucose, 5 mM KCl, 1 mM $MgCl_2$ $H_2O$; adjusted with NaOH to pH 7.4.

Standard growth and passaging procedures used were as follows: Cells were grown in 225 ml flasks. For passaging, cells were washed twice with warm HBSS (5 ml each wash). Two ml of a 0.05% trypsin/EDTA solution was added, the culture was swirled, then the trypsin/DTA solution was aspirated quickly. The culture was then incubated about 2 minutes (until cells lift off), then 10 ml of QT-6 media was added and the cells are further dislodged by swirling the flask and tapping its bottom. The cells were removed and transferred to a 15 ml conical tube, centrifuged at 1000×g for 10 minutes, and resuspended in 10 ml of QT-6 medium. A sample was removed for counting, the cells were then diluted further to a concentration of $1 \times 10^5$ cells/ml using QT-6 medium, and 65 ml of the culture was added per 225 ml flask of passaged cells.

Transfection was accomplished using cDNAs prepared as follows:

For human GlyT2 expression, the pHGT2 clone described in U.S. patent application Ser. No. 08/700,013, filed Aug. 20, 1996, entitled "Human Glycine Transporter," which document is incorporated herein in its entirety by reference.

The human GlyT1a (hGlyT1a) clone contained the sequence of hGlyT1a from nucleotide position 183 to 2108 cloned into the pRc/CMV vector (Invitrogen, San Diego, Calif.) as a Hind III-Xba I fragment as described in Kim et al., *Mol. Pharmacol.*, 45: 608–617, 1994. The first 17 nucleotides (corresponding to the first 6 amino acids) of the GlyT1a sequence reported in this Kim et al. article is actually based on the rat sequence. To determine whether the sequence of human GlyT1a is different in this region, the 5' region of hGlyT1a from nucleotide 1 to 212 was obtained by rapid amplification of cDNA ends using the 5' RACE system supplied by Gibco BRL (Gaithersburg, Md.). Sequencing of this 5' region of GlyT1 a confirmed that the first 17 nucleotides of coding sequence are identical in human and rat GlyT1a.

The human GlyT1b (hGlyT1b) clone contained the sequence of hGlyT1b from nucleotide position 213 to 2274 cloned into the pRc/CMV vector as a Hind III-Xba I fragment as described in Kim et al., supra.

The human GlyT1c (hGlyT1c) clone contained the sequence of hGlyT1c from nucleotide position 213 to 2336 cloned into the pRc/CMV vector (Invitrogen) as a Hind III-Xba I fragment as described in Kim et al., supra. The Hind III-Xba fragment of hGlyT1c from this clone was subcloned into the pRc/RSV vector. Transfection experiments were performed with GlyT1c in both the pRc/RSV and pRc/CMV expression vectors.

The human GlyT1d clone was as described above.

The following four day procedure for the transfections was used:

On day 1, QT-6 cells were plated at a density of $1 \times 10^6$ cells in 10 ml of complete QT-6 medium in 100 mm dishes.

On day 2, the medium was aspirated and the cells were washed with 10 ml of PBS followed by 10 ml of TBS. The TBS was aspirated, then 1 ml of the DEAE/DNA mix was added to the plate. The plate was swirled in the hood every 5 minutes. After 30 minutes, 8 ml of 80 $\mu$M chloroquine in QT-6 medium was added and the culture was incubated for 2.5 hours at 37° C. and 5% $CO_2$. The medium was then aspirated and the cells were washed two times with complete QT-6 medium, then 100 ml complete QT-6 medium was added and the cells were returned to the incubator.

On day 3, the cells were removed with trypsin/EDTA as described above, and plated into the wells of 96-well assay plates at approximately $2 \times 10^5$ cells/well.

On day 4, glycine transport was assayed as described in Example 5.

EXAMPLE 5

Glycine Uptake

This example illustrates a method for the measurement of glycine uptake by transfected cultured cells.

Transient GlyT transfected cells or control cells grown in accordance with Example 4 were washed three times with HEPES buffered saline (HBS). The control cells were treated precisely as the GlyT transfected cells except that the transfection procedure omitted any cDNA. The cells were incubated 10 minutes at 37° C., after which a solution was added containing 50 nM [$^3$H] glycine (17.5 Ci/mmol) and either (a) no potential competitor, (b) 10 mM nonradioactive glycine or (c) a concentration of a prospective agent. A range of concentrations of the prospective agent was used to generate data for calculating the concentration resulting in 50% of the effect (for example, the $IC_{50}$s, which are the concentrations of agent inhibiting glycine uptake by 50%). The cells were then incubated another 20 minutes at 37° C., after which the cells were washed three times with ice-cold HBS. Scintillant was added to the cells, the cells were shaken for 30 minutes, and the radioactivity in the cells was counted using a scintillation counter. Data were compared between the cells contacted or not contacted by a prospective agent, and, where relevant, between cells having GlyT1 activity versus cells having GlyT2 activity, depending on the assay being conducted.

Expression of glycine transporter activity in QT-6 cells transfected with the human GlyT1d clone, phG1d/CMV, is demonstrated in FIG. 2, in which [$^3$H] glycine uptake is shown for mock and phG1d/CMV transfected cells. QT-6 cells transfected with phG1d/CMV show significant increases in glycine transport as compared to mock transfected control cells. The results are presented as means±SEM of a representative experiment performed in triplicate.

Figure 3:
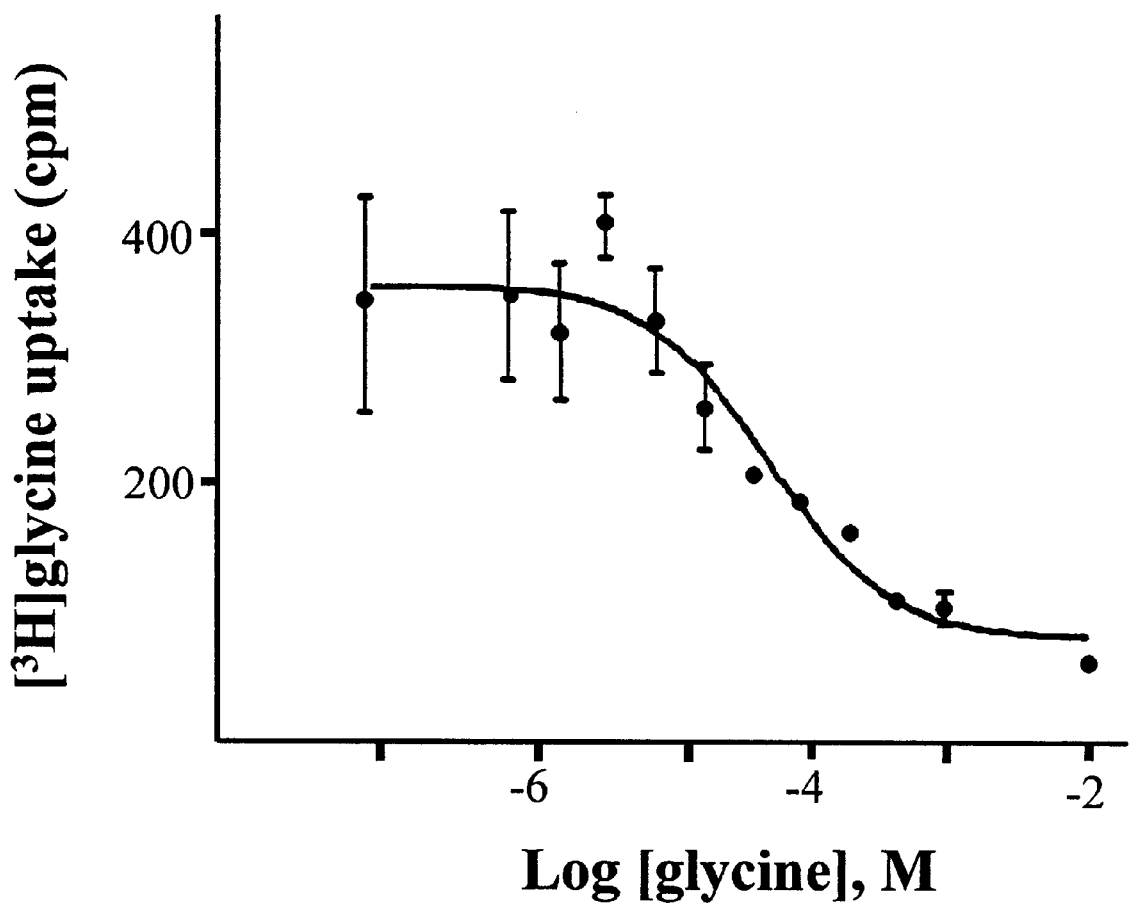
FIG. 3 shows the concentration dependence of GlyT1d mediated transport.

The concentration dependence of glycine transport in phG1d/CMV-transfected cells is shown in FIG. 3. QT-6 cells transfected with the human phG1d/CMV were incubated with 50 nM [$^3$H] glycine and the indicated concentrations of unlabeled glycine for 20 minutes, and the cell-incorporated radioactivity was determined by scintillation counting. Data points represent means±SEM from an experiment performed in quadruplicate. The results indicated an $IC_{50}$ of 60 $\mu$M.

The nucleic acid or amino acid sequences referred to herein by SEQ ID NOs: are as follows:

The nucleic acid sequences described herein, and consequently the protein sequences derived therefrom, have been carefully sequenced. However, those of ordinary skill will recognize that nucleic acid sequencing technology can be susceptible to some error. Those of ordinary skill in the relevant arts are capable of validating or correcting these sequences based on the ample description herein of methods of isolating the nucleic acid sequences in question, and such modifications that are made readily available by the present disclosure are encompassed by the present invention. Furthermore, those sequences reported herein are within the invention whether or not later clarifying studies identify sequencing errors.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method for the analysis of or screening for an agent that is an enhancer or inhibitor of glycine transport, the method comprising: (a) providing a first and second assay composition comprising isolated host cells expressing an exogenous nucleic acid encoding a glycine transporter protein, wherein the encoded glycine transporter protein comprises an amino acid sequence as set forth in SEQ ID NO: 2 or an amino acid sequence that has six or fewer amino acid changes relative to the amino acid sequence as set forth in SEQ ID NO: 2; (b) contacting the first assay composition with the agent and; (c) measuring the amount of glycine transport exhibited by the first assay composition as compared with the second assay composition that has not been contacted with the agent, in order to screen for the enhancement or inhibition of glycine transport.

2. The method of claim 1, wherein the encoded glycine transporter protein comprises an amino acid sequence that has three or fewer amino acid changes relative to the amino acid sequence as set forth in SEQ ID NO: 2.

3. The method of claim 1, wherein the encoded glycine transporter protein comprises an amino acid sequence that has one amino acid change relative to the amino acid sequence as set forth in SEQ ID NO: 2.

4. The method of claim 1, wherein the encoded glycine transporter protein comprises an amino acid sequence as set forth in SEQ ID NO: 2.

5. A purified glycine transporter protein comprising an amino acid sequence as set forth in SEQ ID NO: 2 or an amino acid sequence that has six or fewer amino acid changes relative to the amino acid sequence as set forth in SEQ ID NO: 2.

6. The purified glycine transporter protein of claim 5, wherein the glycine transporter protein comprises an amino acid sequence that has three or fewer amino acid changes relative to the amino acid sequence as set forth in SEQ ID NO: 2.

7. The purified glycine transporter protein of claim 5, wherein the glycine transporter protein comprises an amino acid sequence that has one amino acid change relative to the amino acid sequence as set forth in SEQ ID NO: 2.

8. The purified glycine transporter protein of claim 5, wherein the glycine transporter protein comprises an amino acid sequence as set forth in SEQ ID NO: 2.

9. A composition comprising isolated membranes obtained from heterologous host cells expressing an exogenous nucleic acid encoding a glycine transporter protein, wherein the encoded glycine transporter protein comprises an amino acid sequence as set forth in SEQ ID NO: 2 or an amino acid sequence that has six or fewer amino acid changes relative to the amino acid sequence as set forth in SEQ ID NO: 2.

10. The encoded glycine transporter protein of claim 9, wherein the glycine transporter protein comprises an amino acid sequence that has three or fewer amino acid changes relative to the amino acid sequence as set forth in SEQ ID NO: 2.

11. The encoded glycine transporter protein of claim 9, wherein the glycine transporter protein comprises an amino acid sequence that has one amino acid change relative to the amino acid sequence as set forth in SEQ ID NO: 2.

12. The encoded glycine transporter protein of claim 9, wherein the glycine transporter protein comprises an amino acid sequence as set forth in SEQ ID NO: 2.

* * * * *